(12) United States Patent
Davis et al.

(10) Patent No.: US 7,306,765 B2
(45) Date of Patent: Dec. 11, 2007

(54) APPARATUS AND METHOD FOR CHEMICAL ANALYSIS

(75) Inventors: Bruce R. Davis, Seattle, WA (US); Thomas C. Foulds, Renton, WA (US); Terry C. Tomt, Enumclaw, WA (US)

(73) Assignee: The Boeing Company, Chicago, IL (US)

( * ) Notice: Subject to any disclaimer, the term of this patent is extended or adjusted under 35 U.S.C. 154(b) by 842 days.

(21) Appl. No.: 10/620,071

(22) Filed: Jul. 15, 2003

(65) Prior Publication Data

US 2005/0014271 A1    Jan. 20, 2005

(51) Int. Cl.
*G01N 31/00* (2006.01)
(52) U.S. Cl. ........................ 422/62; 422/103; 422/100; 422/67; 422/68.1; 436/180
(58) Field of Classification Search ................ 422/100, 422/103, 50, 62, 67, 68.1; 436/180
See application file for complete search history.

(56) References Cited

U.S. PATENT DOCUMENTS

| | | | | |
|---|---|---|---|---|
| 4,055,751 | A * | 10/1977 | Bussmann et al. | 700/266 |
| 4,108,602 | A * | 8/1978 | Hanson et al. | 436/52 |
| 4,520,108 | A * | 5/1985 | Yoshida et al. | 436/52 |
| 5,308,583 | A * | 5/1994 | Sanuki | 422/100 |
| 5,405,585 | A * | 4/1995 | Coassin | 422/100 |
| 5,416,023 | A * | 5/1995 | Binder et al. | 435/287.9 |
| 5,508,200 | A | 4/1996 | Tiffany et al. | |
| 6,162,644 | A * | 12/2000 | Choi et al. | 436/55 |
| 6,344,172 | B1 * | 2/2002 | Afeyan et al. | 422/70 |
| 6,869,799 | B1 * | 3/2005 | Guan et al. | 436/37 |
| 6,902,704 | B2 * | 6/2005 | Wilson | 422/100 |
| 6,979,569 | B1 * | 12/2005 | Carver et al. | 436/63 |
| 6,998,095 | B2 * | 2/2006 | Anderson et al. | 422/103 |
| 2001/0051110 | A1 * | 12/2001 | Borade et al. | 422/99 |
| 2002/0164821 | A1 * | 11/2002 | Brink et al. | 436/180 |
| 2003/0224532 | A1 * | 12/2003 | Smith et al. | 436/180 |

* cited by examiner

*Primary Examiner*—Brian R. Gordon
(74) *Attorney, Agent, or Firm*—Alston & Bird LLP

(57) ABSTRACT

An apparatus and method for chemically analyzing a sample fluid are provided. The apparatus includes two fluid selection valves with multiple input ports for selectively receiving sample and reagent fluids. The selection valves are configured to selectively connect the input ports to output ports such that the sample and reagent fluids can be delivered through a fluid injection valve to a sample vessel and therefrom to an analysis device. The analysis device is configured to receive the sample and reagent fluids and determine at least one chemical characteristic of the sample fluid.

25 Claims, 3 Drawing Sheets

APPARATUS AND METHOD FOR CHEMICAL ANALYSIS

BACKGROUND OF THE INVENTION

1) Field of the Invention

The present invention relates to the analysis of chemicals and, in particular, to an apparatus and method for automated chemical analysis of sample fluids, such as samples of a solution for metal processing.

2) Description of Related Art

Chemical analysis is a requirement for a variety of different processes, including the manufacture of chemicals, the chemical treatment of metals, and the like. For example, in a typical aluminum chemical milling process, an aluminum workpiece is selectively exposed to a hot, caustic chemical etchant such as sodium hydroxide. The sodium hydroxide can be provided in an etching solution in a vat in which the aluminum workpiece is immersed. The sodium hydroxide reacts with the aluminum of the workpiece, and material is chemically removed, i.e., etched, from the exposed surfaces of the workpiece. As the etching of multiple workpieces occurs, the content of sodium hydroxide in the etching solution is reduced and the content of aluminum in the solution increases. The decrease in sodium hydroxide and the increase in aluminum decrease the etching effectiveness of the solution, requiring longer periods for etching.

To improve the effectiveness of the process, the etching solution can be replaced, or a regeneration process can be conducted to restore the sodium hydroxide to the solution and remove the aluminum from the solution. Typically, the solution is tested periodically to determine if the solution should be replaced or regenerated. For example, a chemical test can be performed to determine the content of the sodium hydroxide and/or the aluminum in the solution. If regeneration of the solution is to be performed, the information regarding the content of the solution can also be used to determine how the regeneration process should be performed. For example, the volume of sodium hydroxide and other chemicals that are added to the solution during regeneration can be determined according to the content of the solution when regeneration occurs. Testing of the solution is typically performed manually by a technician. The technician must go to the site of the etching process, remove a sample of the solution, and take the sample to a lab for testing. The testing process is labor-intensive and time-consuming. Further, during the delay required for testing, the content of the solution may change, thereby decreasing the accuracy of the results.

Thus, there exists a need for an apparatus and method for automatically chemically analyzing sample fluids. The apparatus and method should not be overly complex and should preferably provide results quickly and accurately. In addition, the apparatus should be capable of analyzing a plurality of solutions, such as the various solutions used in or resulting from an etching process. Further, the apparatus should be capable of storing and/or communicating the results of the analysis, for example, to a remote user.

BRIEF SUMMARY OF THE INVENTION

The present invention provides an apparatus and method for automatically chemically analyzing sample fluids. The apparatus can be configured to receive a plurality of sample and reagent fluids, for example, from a chemical etching process. The apparatus can be connected to a processing device that can control the analyses and can store and communicate the results, for example, via a communication network to a remote user.

According to one embodiment of the present invention, the apparatus includes first and second fluid selection valves. The first valve is configured to selectively fluidly connect a plurality of sample input ports to a sample output port so that sample fluids received through the input ports can be delivered to the output port. The second valve is configured to selectively fluidly connect a plurality of reagent input ports to a reagent output port so that reagent fluids received through the input ports can be delivered to the output port. A fluid injection valve, which is adjustable between first and second positions, is configured to receive the sample and reagent fluids from the first and second selection valves. A sample vessel is fluidly connected to the fluid injection valve, and an analysis device is connected to the injection valve via the sample vessel. In the first position the fluid injection valve connects the sample output port to the sample vessel, and in the second position the fluid injection valve connects the reagent output port to the sample vessel so that the sample and reagent fluids can be injected into the sample vessel. The analysis device is configured to receive the sample and reagent fluids from the fluid injection valve and determine at least one chemical characteristic of the sample fluid.

For example, the fluid injection valve in the first position can fluidly connect the sample output port to an exhaust outlet via the sample vessel so that the sample fluid is delivered through and fills the sample vessel. The fluid injection valve in the second position can fluidly connect the reagent output port to the analysis device via the sample vessel so that fluid in the sample vessel is delivered to the analysis device. The first and/or second fluid selection valves can also have a rinse fluid input port that is connected to a source of rinse fluid such as water. Either of the fluid selection valves can also have an evacuation input port that can be connected by the fluid injection valve to the analysis device so that the analysis device can be evacuated to the selection valve. First and second pumps can be selectively connected by the fluid injection valve to the sample vessel.

According to one aspect of the present invention, an optical device is configured to optically analyze a fluid in the analysis device and determine at least one chemical characteristic thereof. A processing device in communication with the analysis device can be configured to process an output of the analysis device and indicate a chemical characteristic of the sample fluid on a display device. The processing device and/or the display device can be electronically connected to a communication network, for example, by Ethernet connections.

A mixer can be configured to mix a fluid in the analysis device, and a bubble detector can be configured to detect the presence of gas in a fluid being sampled. A standard sample source can be fluidly connected to the first fluid selection valve and configured to supply a standard sample having a predetermined chemical characteristic.

The present invention also provides a method of chemically analyzing a sample fluid. The method includes adjusting a first fluid selection valve to fluidly connect a select sample input port to a sample output port such that a select sample fluid is delivered from the sample input port to the output port. The fluid injection valve is adjusted to a first position so that the valve fluidly connects the sample output port to a sample vessel. The select sample fluid is delivered from the sample output port to the sample vessel. The fluid injection valve is adjusted to a second position such that the valve fluidly connects a reagent input port to the sample vessel. A reagent fluid is delivered from the reagent input port to the analysis device via the sample vessel such that a predetermined amount of the sample fluid is delivered to the analysis device. At least one chemical characteristic of the sample fluid is determined in the analysis device, for example, by detecting an optical characteristic of the sample fluid. The fluids can be delivered to the analysis device by one or more pumps. The presence of gas in the fluids passing through the sample vessel can be detected, and the sample and reagent fluids can be mixed in the analysis device.

The fluid injection valve is then adjusted to the first position, thereby fluidly connecting the analysis device to an exhaust outlet so that the sample fluid in the analysis device is exhausted therefrom. The fluid injection valve is adjusted to the second position, thereby fluidly connecting the sample vessel to a rinse fluid source so that the rinse fluid source is delivered to the sample vessel. When the fluid injection valve is adjusted to the second position, the analysis device can also be connected to the exhaust outlet via the sample vessel. When the fluid injection valve is adjusted to the first position, one of the fluid selection valves can connect a rinse fluid input port to the sample vessel via the fluid injection valve.

According to one aspect of the invention, an output signal of the analysis device is delivered to a processing device and a chemical characteristic of the sample fluid is displayed on a display device. Further, a signal representative of a characteristic of the sample fluid can be communicated via a communication network, for example, via one or more Ethernet ports.

The sample fluid can be a standard sample that has a predetermined chemical characteristic, for example, to calibrate the analysis device. Further, the standard sample can be delivered and analyzed in first and second predetermined amounts for calibration.

BRIEF DESCRIPTION OF THE SEVERAL VIEWS OF THE DRAWINGS

Figure 1:
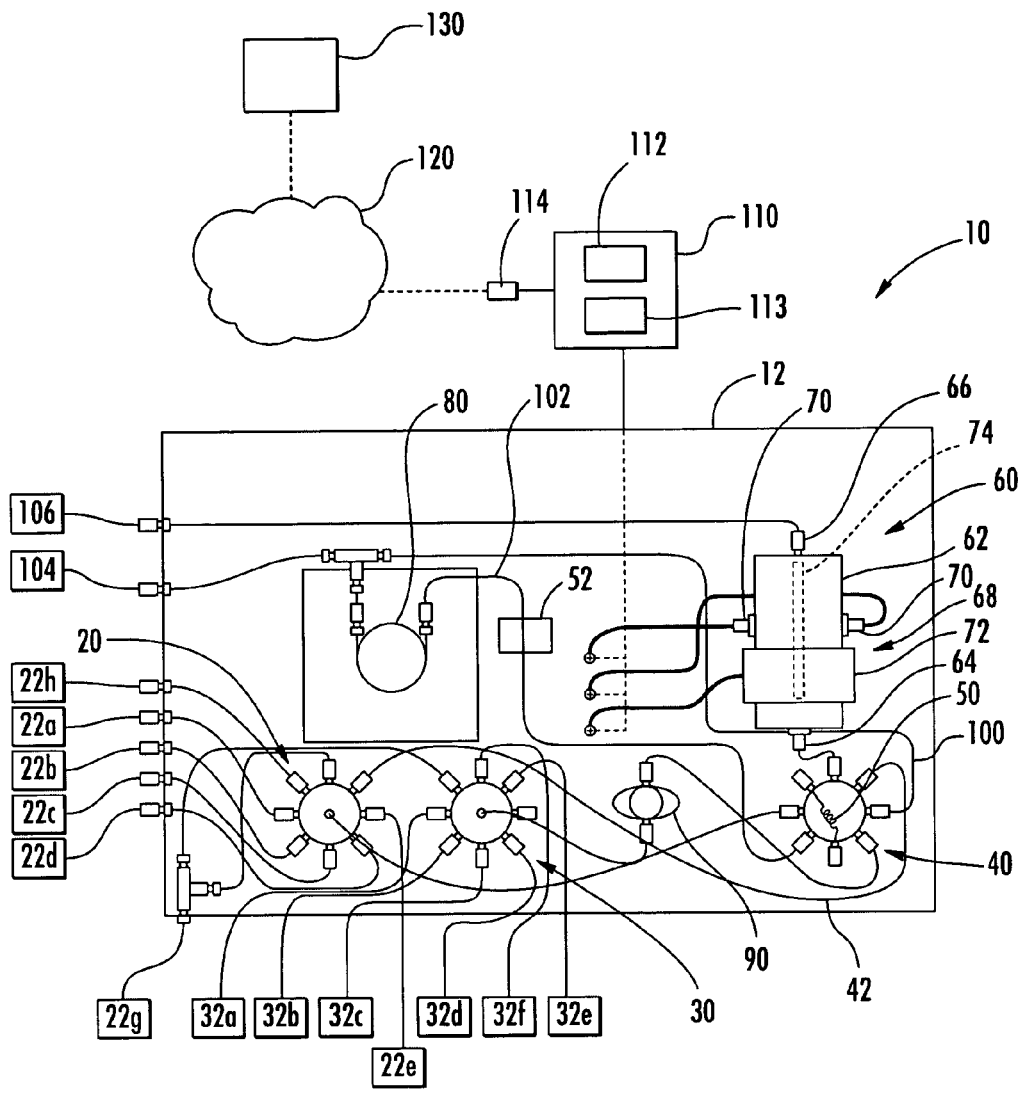
Figure 1A:
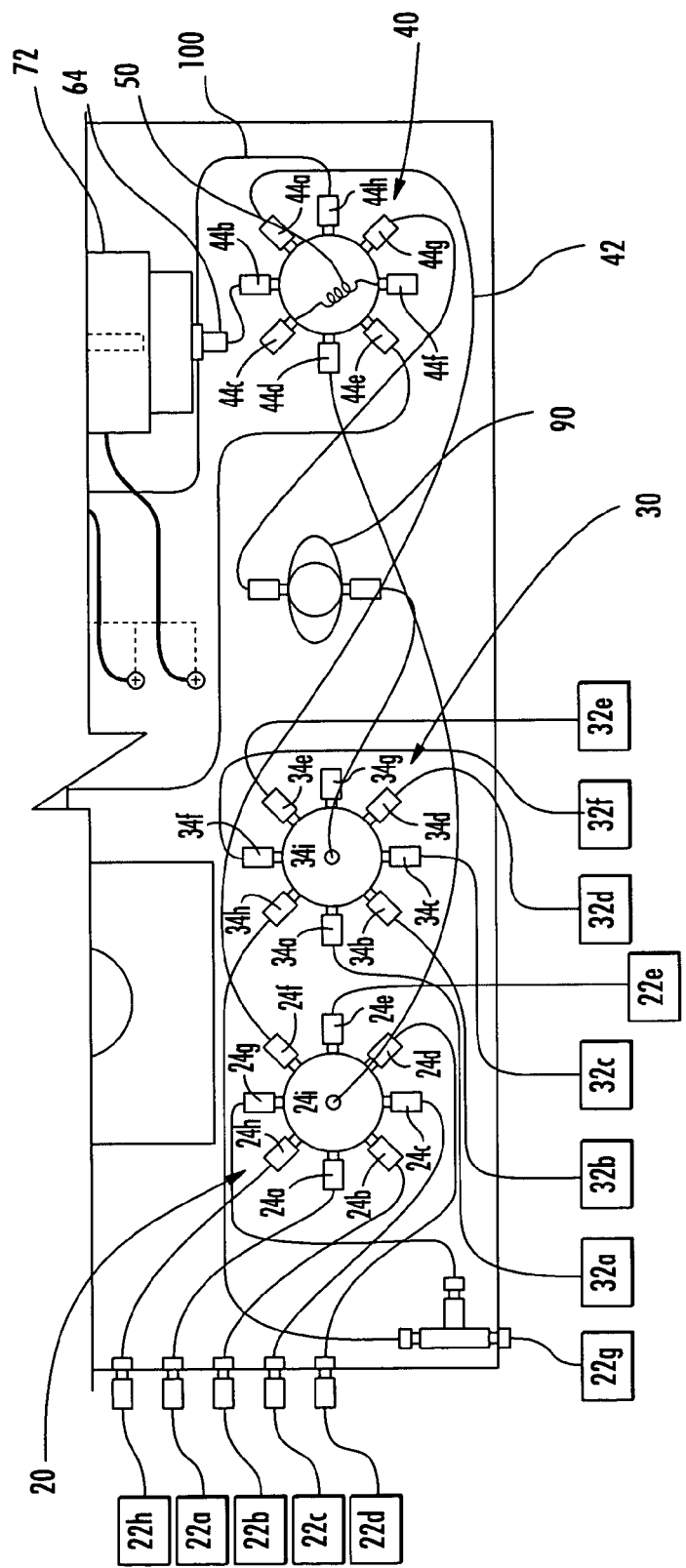
Figure 2:
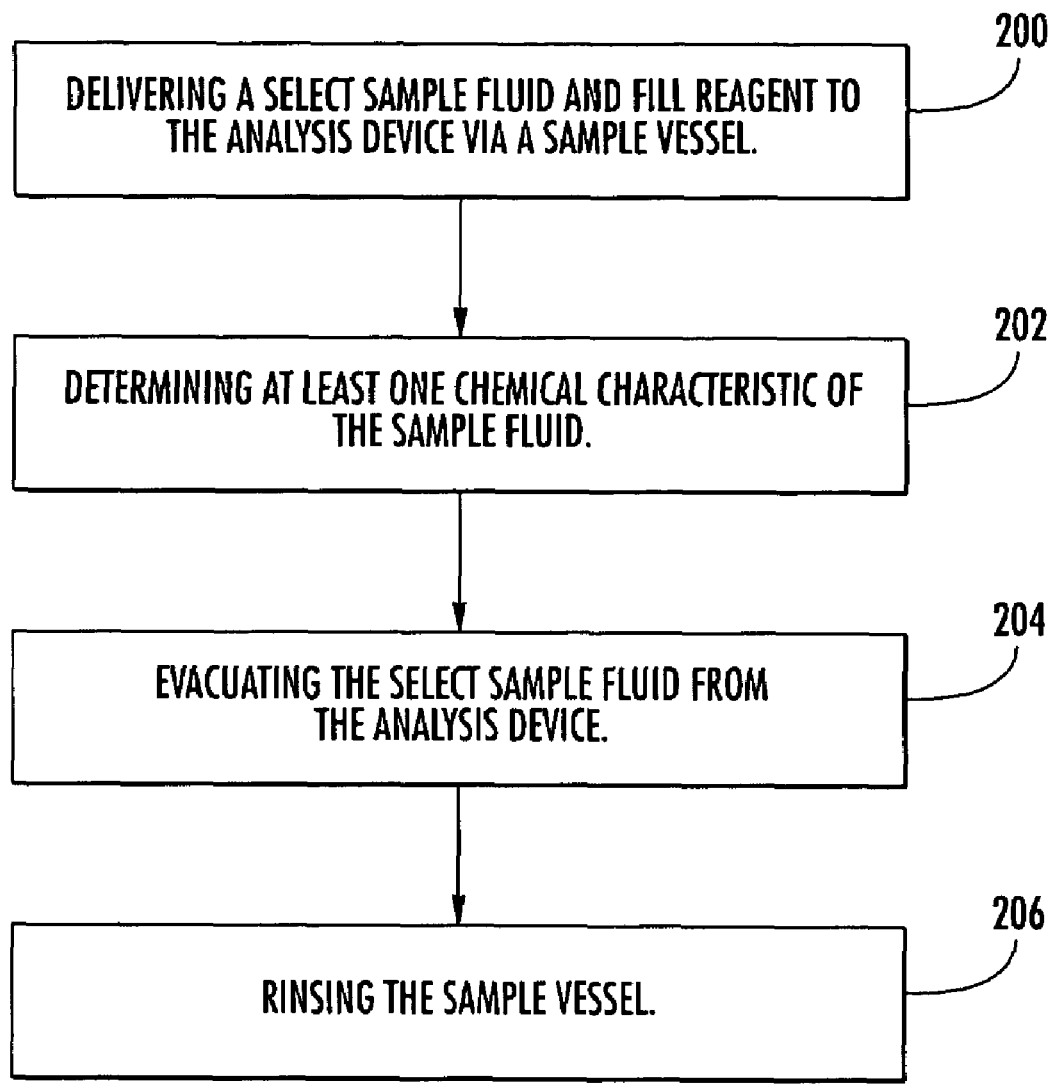

Having thus described the invention in general terms, reference will now be made to the accompanying drawings, which are not necessarily drawn to scale, and wherein:

FIG. 1 is a schematic view illustrating an apparatus for chemically analyzing a sample fluid according to one embodiment of the present invention;

FIG. 1A is an enlarged schematic view illustrating the valves of the apparatus of FIG. 1; and FIG. 2 is a flow diagram illustrating the operations for chemically analyzing a sample fluid according to one embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Referring now to the drawings, and in particular to FIG. 1, there is shown an apparatus 10 for chemically analyzing a sample fluid. The apparatus 10 can be used for analyzing a variety of substances. For example, the apparatus 10 can be used to detect the presence or quantity of one or more particular chemicals in a sample fluid during a chemical process. According to one embodiment of the present invention, the apparatus 10 is used in conjunction with a chemical milling or etching process to detect the content of an etchant chemical and etched structural material in an etching fluid used to process a workpiece. The apparatus 10 can be configured to receive a plurality of sample fluids so that the apparatus 10 can selectively analyze each of the sample fluids. Further, the apparatus 10 can be configured to receive a plurality of reagents for performing various analyses on the sample fluids.

The sample fluids are supplied by sources 22a-22d, which are fluidly connected to a first fluid selection valve 20. In FIGS. 1 and 1A, the four sample fluid sources 22a-22d are connected to sample input ports 24a-24d of the first fluid selection valve 20. Except where otherwise noted, the connections between the components of the apparatus 10 are fluid connections, which can be effected by pipes, tubes, hoses, fluid connectors, and other conventional fluid connection devices. Additional input ports 24e-24h can be configured to receive other fluids, for example, a standard sample, a return fluid, water from a rinse source 22g, and an auxiliary fluid, respectively. The standard sample, provided from source 22e such as a vessel, can have predetermined chemical characteristics such that the standard sample can be used for calibrating the apparatus 10. The return fluid can be received from another device in the apparatus 10, as described further below. Port 24h can be reserved for temporary use with an additional sample fluid or otherwise used to receive auxiliary fluids from an auxiliary source 22h. The first fluid selection valve 20 is configured to selectively connect each of the input ports 24a-24h to a sample output port 24i. The valve 20 can be an electronically controlled device such as the Model C25 stream selector available from Valco Instruments Co. Inc. of Houston, Tex., which selectively connects each of eight input ports to an output port. In other embodiments, other selection valves can be used, and the selection valve 20 can have a greater or lesser number of input ports.

A plurality of reagent sources 32a-32f provide reagent fluids for mixing with the sample fluids. Each reagent fluid can be formulated to react with one or more of the sample fluids to affect a measurable attribute of the sample fluid according to a chemical characteristic of the sample fluid. For example, the reagent fluids can affect the color or other physical attributes of the sample fluids according to the presence and/or quantity of particular chemicals in the sample fluids. According to one typical titration operation, a first reagent, hereinafter referred to as a fill reagent, is chemically reacted with the sample fluid, and a second reagent, hereinafter referred to as the titration reagent, is then used to "indicate" the reaction therebetween. The reagent sources 32a-32f are connected to reagent input ports 34a-34f of a second fluid selection valve 30. Port 34g of the second valve 30 can be reserved for receiving additional reagents or other fluids. Port 34h is fluidly connected to a rinse source, for example, the same water source 22g connected to port 24g of the first valve 20. The second fluid selection valve 30, which can be structurally similar or identical to the first fluid selection valve 20, is configured to selectively connect each of the input ports 34a-34h to a reagent output port 34i of the valve 30.

Both of the fluid selection valves 20, 30 are fluidly connected to a fluid injection valve 40. The fluid injection valve 40 includes a plurality of ports 44a-44h and is configured to selectively connect the ports 44a-44h. The fluid injection valve 40 illustrated in FIGS. 1 and 1A is adjustable between first and second positions. In the first position, the fluid injection valve 40 establishes four fluid connections and, in particular, fluidly connects the following pairs of ports: port 44a to port 44b, port 44c to port 44d, port 44e to port 44f, and port 44g to port 44h. In the second position, the fluid injection valve fluidly connects port 44b to port 44c, port 44d to port 44e, port 44f to port 44g, and port 44h to port 44a.

Port 44a is fluidly connected to a return line 42 that is connected to the return input port 24f of the first fluid selection valve 20. Port 44b is fluidly connected to an analysis device 60. Ports 44c and 44f are each fluidly connected to opposite ends of a sample vessel 50, for example, a tube having a predetermined volume. Port 44d is connected to the output port 24i of the first fluid selection valve 20. Port 44e is fluidly connected to a first pump 80 configured to exhaust fluids from the apparatus 10, for example, to an exhaust outlet such as a waste receptacle 104. Port 44g is fluidly connected to the output port 34i of the second fluid selection valve 30 via a second pump 90. Port 44h is fluidly connected to an exhaust line 100, which exhausts to the waste receptacle 104. Thus, in the first position, the fluid injection valve 40 connects the output port 24i of the first fluid selection valve 20 to the first pump 80 via the sample vessel 50, and the analysis device 60 is fluidly connected to the return input port 24f of the first fluid selection valve 20. In the second position, the fluid injection valve 40 connects the output port 34i of the second fluid selection valve 30 via the second pump 90 to the sample vessel 50 and therethrough to the analysis device 60.

The analysis device 60 is configured to receive the sample and reagent fluids and determine at least one chemical characteristic of the sample fluids. The analysis device 60 can include a vessel 62 that is formed of a chemical resistant material such as Plexiglas®, a registered trademark of Rohm and Haas Company Corp. The vessel 62 has a port 64 through which the fluids can be delivered and exhausted and can also have an additional exhaust port 66 that is fluidly connected to an exhaust outlet such as waste receptacle 106. The analysis device 60 can also include a mixer 68 and one or more detection devices such as fiber optic probes 70. The mixer 68 can be a device that mixes the fluids in the vessel 62 by stirring, agitating, or otherwise imparting motion to the contents of the analysis device 60. For example, the mixer 68 can include an electromagnetic mixer base 72 configured to electromagnetically actuate a stir bar 74 disposed within the vessel 62.

The fiber optic probes 70 are configured to determine a color or other attribute of the sample fluid in the analysis device 60. The probes 70 can be rod-shaped devices, such as FIA-P400 fiber optic devices available from Ocean Optics Inc. of Dunedin, Fla., and the probes 70 can extend proximate to or into the vessel 62 of the analysis device 60. Further, the position of one or both of the probes 70 can be adjustable so that the distance between the probes 70 can be modified to adjust the path length of light through the vessel 62. A predetermined quantity of the sample fluid can be mixed in the analysis device 60 and titrated by adding one of the reagents until a specific chemical reaction occurs, which can be indicated by a change in color or other attribute of the sample fluid. The fiber optic probes 70 can be used to detect attributes of the sample fluid by transmitting light of one or more wavelengths through the sample fluid, receiving the light transmitted therethrough, and determining the optical attribute of the sample fluid according to the light transmission or absorption characteristics of the sample fluid.

The operations for testing a sample fluid according to one embodiment of the present invention are illustrated in FIG. 2. It is understood that additional operations can be performed and/or some of the described operations can be omitted without departing from the scope of the present invention. In Block 200, a select sample fluid and fill reagent are delivered to the analysis device 60 via the sample vessel 50. For example, the first fluid selection valve 20 is adjusted to select one of the sample fluids, and the respective sample input port 22a-22d is fluidly connected by the valve 20 to the output port 24i thereof. The fluid injection valve 40 is adjusted to the first position so that the select sample fluid can be delivered from the output port 24i, through ports 44d and 44c of the fluid injection valve 40, and into the sample vessel 50. The sample vessel 50 is also fluidly connected, via ports 44f and 44e, to the first pump 80, which pumps the select sample fluid from the source, through the first fluid selection valve 20, through the fluid injection valve 40 and the sample vessel 50, to be exhausted from the apparatus 10 through an exhaust line 102. Thus, as the first pump 80 is operated, the select sample fluid fills the sample vessel 50 and is exhausted therefrom. The flow of the sample fluid can be continued until the sample vessel 50 is sufficiently flushed with the sample fluid, i.e., other fluids previously in the sample vessel 50 are exhausted therefrom and the sample vessel 50 is filled with the select sample fluid. Further, a bubble detector 52 can monitor the fluid passing through the sample vessel 50, e.g., in the exhaust line 102, so that the bubble detector 52 determines if there are bubbles of air or other gases in the sample fluid that may affect the analysis.

The second fluid selection valve 30 is adjusted to connect one of the reagent input ports 34a-34f to the output port 34i, and the fluid injection valve 40 is adjusted to the second position. Thus, the second pump 90 can be actuated to deliver the select reagent, i.e., the fill reagent, to the sample vessel 50 via ports 44g and 44f. The sample vessel 50 is also connected to the analysis device 60 via ports 44c and 44b. Thus, as the pump 90 delivers the fill reagent to the sample vessel 50, the select sample fluid in the sample vessel 50 is delivered from the sample vessel 50 through ports 44c and 44b to the analysis device 60. The pump 90 continues to deliver the fill reagent to the analysis device 60 until a predetermined volume of the sample fluid and the fill reagent are disposed in the analysis device 60. For example, the fill reagent can be delivered to the analysis device 60 until the sample fluid and fill reagent in the analysis device 60 reach and exceed the level of the fiber optic probes 70. Alternatively, the pump 90 or another metering device can be used to meter the amount of the sample and reagent fluids delivered to the analysis device 60 so that the predetermined volume is delivered. The mixer 68 is used to mix the sample fluid and the fill reagent in the analysis device 60 during and/or after the predetermined volume of fluid is delivered to the analysis device 60.

Next, in Block 202, the analysis device 60 is used to determine a chemical characteristic of the sample fluid. According to one embodiment of the present invention, the apparatus 10 is used to perform a titration of the sample fluid. For example, the second fluid selection valve 30 can be adjusted to connect one of the reagent sources 32a-32f to the output port 34i to provide the corresponding reagent, i.e., the titration reagent, to the output port 34i. The pump 90 delivers the titration reagent through the fluid selection valve 30 and the sample vessel 50 to the analysis device 60. The mixer 68 can be used to mix the titration reagent with the sample fluid and the fill reagent to form a test fluid in the analysis device 60. In addition, one of the fiber optic probes 70 can be energized to emit light through the fluid in the analysis device 60, and the other fiber optic probe 70 can be used to detect the light transmitted through the test fluid. The light emitted by the fiber optic probes 60 can be of a predetermined wavelength. Alternatively, multi-wavelength light can be emitted, and light of one or more wavelengths can be measured and analyzed as described below.

A signal, such as an electronic or optic signal, from the fiber optic probes 70 can be communicated to a computer or other processing device 110. The analysis device 60 and/or the processing device 110 monitors the signal from the fiber optic probes 70 and determines if an attribute such as the color of the test fluid changes, thereby indicating a chemical reaction characteristic of the titration reagent. For example, the processing device 110 can include a spectrometer 113 configured to receive an optical signal from the fiber optic probes 70, spectrally analyze the signal from the probes 70 to determine the transmission and absorption of the light in the analysis device 60, and communicate that data as an electronic signal to other components of the processing device 110. Thus, the processing device 110 can transduce the optical signal from the fiber optic probes 70 to an electronic signal and determine a characteristic of the sample fluid. For example, the processing device 110 can use known titration algorithms to determine the quality or quantity of a chemical in the sample fluid according to the reaction that occurs with the titration reagent and/or the amount of the titration reagent that is injected before the reaction occurs. The amount of the titration reagent delivered to the analysis device 60 can be determined by monitoring the pump 90 or other metering device (not shown) or by detecting the change of the fluid level in the vessel 62 of the analysis device 60.

In Block 204, the analysis device 60 is exhausted by adjusting the fluid injection valve 40 to the first position, and adjusting the first fluid selection valve 20 to fluidly connect the return port 24$f$ to the output port 24$i$. Thus, the first pump 80 can be used to deliver the test fluid from the analysis device 60, through ports 44$b$ and 44$a$, through the return line 42, through port 24$f$ to the output port 24$i$, through ports 44$d$ and 44$c$ to the sample vessel 50, through ports 44$f$ and 44$e$ to the first pump 80, and exhausted therefrom through line 102.

In Block 206, a rinse operation can be performed to further remove any remaining test fluid in the analysis device 60 and/or the sample vessel 50. The rinse operation can be performed by adjusting the fluid injection valve 40 to the second position, and adjusting the second fluid selection valve 30 to connect the water source 22$g$ through port 34$h$ to the output port 34$i$. Thus, as the second pump 90 is operated, the water is delivered from the water source 22$g$, through port 34$h$ and the output port 34$i$ of the second fluid selection valve 30, through the second pump 90, through ports 44$g$ and 44$f$ to the sample vessel 50, through ports 44$c$ and 44$b$, and into the analysis device 60. The analysis device 60 can be partially filled or completely filled with water. The pump 90 can force the water through the exhaust port 66 of the analysis device 60. Further, the analysis device 60 can be repeatedly rinsed with water and exhausted.

The apparatus 10 can also be calibrated for example, on a daily or other periodic basis. Calibration can be performed by testing sample fluids with known characteristics, such as the standard sample provided through port 24$e$ of the first fluid selection valve 20. If the measured characteristic that is determined by the apparatus 10 for the standard sample differs from the known characteristic value, the apparatus 10 can be calibrated accordingly. In addition, the calibration can be based on multiple calibration tests that are performed for two or more standard samples. Alternatively, a single standard sample can be used to conduct multiple calibration tests. For example, the sample vessel 50 can be filled with the standard sample from source 22$e$ by the process described above so that a volume of the standard sample equal to the predetermined volume of the vessel 50, for example 50 μL, is delivered to the analysis device 60 for analysis. Subsequently, the analysis device 60 can be emptied for a second calibration test in which the sample vessel 50 is filled with 50 μL of the same standard sample, the standard sample is delivered to the analysis device 60, and then the sample vessel 50 is filled again so that an additional 50 μL of the standard sample is delivered to the analysis device 60 for analysis. The second calibration test is performed with twice as much of the standard sample in the analysis device 60 and, hence, the content of each of the components of the standard sample should be twice as much as during the first calibration test. Thus, two or more data points for calibrating the apparatus 10 can be derived from the subsequent analyses of a single standard fluid.

As shown in FIG. 1, an enclosure 12 can be provided for the apparatus 10, and the enclosure 12 can protect the components of the apparatus 10 from the working environment of the apparatus 10. The sample fluids received through the sample ports 24$a$-24$d$ can be provided through pipes or tubes from a chemical process, and the apparatus 10 can be positioned proximate to the equipment used for that process.

A display device 112, such as a cathode ray tube or LCD screen, can be provided with the apparatus 10 for displaying the chemical determinations that result from the tests performed by the apparatus 10. Further, the processing device 110 can be in communication with a communication network 120, for example, a local area network and/or the World Wide Web so that one or more characteristics of the sample fluids can be communicated to users at remote locations and/or so that the apparatus 10 can be controlled by users at remote locations via one or more remote computing devices 130. The processing device 110 can include an Ethernet connection 114, or other conventional connection devices, to provide compatibility with conventional network equipment. In addition, the processing device 110 can provide a scheduling function by controlling the operations of the apparatus 10 at predetermined times. For example, the processing device 110 can be programmed to control the apparatus 10 to test one or more of the sample fluids at predetermined times, perform self-calibration operations at predetermined times, and the like. Further the processing device 110 can store results of the tests and/or analyze the results of successive tests to determine trends or to cumulate statistical data for multiple tests.

According to one embodiment of the present invention, the apparatus 10 is used in conjunction with a chemical milling process in which material is selectively removed or etched from a workpiece. The workpiece is masked, or partially covered, with a resistant material so that the select portions of the member are exposed. The workpiece is then immersed in a caustic etching fluid that dissolves material from the surface of the exposed portions, thereby etching the member. For example, a workpiece formed of aluminum or an aluminum alloy can be etched in an etching fluid that includes an etchant chemical such as sodium hydroxide. The etch rate is affected by the concentration of the etchant chemical, the concentration of dissolved structural material from the workpiece, and the temperature of the etching fluid. Generally, the etch rate increases with higher concentrations of etchant chemical and higher temperatures and decreases with higher concentrations of dissolved structural material. The etching fluid can also include sodium sulfide, which generally tends to decrease the roughness of the etched portions of the workpiece by removing from solution alloy metals such as magnesium, zinc, or copper in the workpiece that can otherwise redeposit on the workpiece.

As the workpiece is etched by the sodium hydroxide in the etching fluid, the concentration of aluminum increases, and the concentration of sodium hydroxide decreases. The etching fluid can be used until the aluminum content exceeds a predetermined maximum and/or the sodium hydroxide content is reduced below a predetermined minimum such that the etching effectiveness of the etching fluid is below a minimum acceptable level. The etching fluid can be replaced, or a regeneration system can be used to remove the aluminum from the etching fluid and add sodium hydroxide thereto. In either case, the apparatus 10 can be used to determine the concentration of aluminum and sodium hydroxide in the etching fluid to determine when the etching fluid should be replaced or regenerated. Additionally, data regarding the contents of the etching fluid can used to determine the appropriate regeneration process for the etching fluid.

For example, the apparatus 10 can use a pH indicator, such as the conventional Nile Blue indicator, as the fill reagent and sulfosalicylic acid as the titration reagent during a test to determine the sodium hydroxide content in an etching fluid. The aluminum content in the etching fluid can be determined using a 0.5M sodium fluoride solution as the fill reagent and 45 g/L sulfosalicylic acid, 0.0008% Chlorophenol Red indicator as the titration reagent, and detecting the transmittance of light with wavelength of 578 nm with the fiber optic probes 70. The sodium sulfide content can be determined using 0.5 g/L sodium nitroprusside as the fill reagent and 3 g/L potassium ferricyanide as the titration reagent, and detecting the color transition of the nitroprusside at 525 nm with the fiber optic probes 70.

Many modifications and other embodiments of the invention set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for chemically analyzing a sample fluid, the apparatus comprising:
    a first fluid selection valve having a plurality of sample input ports and a sample output port, the first fluid selection valve being configured to selectively fluidly connect each of the sample input ports to the sample output port, and each sample input port being configured to receive a sample fluid;
    a second fluid selection valve having a plurality of reagent input ports and a reagent output port, the second fluid selection valve being configured to selectively fluidly connect each of the reagent input ports to the reagent output port, and each reagent input port being configured to receive a reagent fluid;
    a fluid injection valve adjustable between first and second positions, the fluid injection valve being configured to receive the sample and reagent fluids from the sample output port of the first fluid selection valve and the reagent output port of the second fluid selection valve;
    a sample vessel fluidly connected to the fluid injection valve and configured to receive the sample fluids therefrom;
    an analysis device fluidly connected to the injection valve via the sample vessel and configured to receive the sample and reagent fluids from the fluid injection valve, the analysis device configured to determine at least one chemical characteristic of the sample fluid; and
    a mixer configured to mix fluids in the analysis device,
    wherein the fluid injection valve in the first position fluidly connects the sample output port to the sample vessel such that the sample fluids can be injected into the sample vessel, and the fluid injection valve in the second position fluidly connects the reagent output port to the sample vessel such that the reagent fluids can be injected into the sample vessel.

2. An apparatus according to claim 1, further comprising an exhaust outlet, wherein the fluid injection valve in the first position fluidly connects the sample output port to the exhaust outlet via the sample vessel, and the fluid injection valve in the second position fluidly connects the reagent output port to the analysis device via the sample vessel.

3. An apparatus according to claim 1, further comprising a source of rinse fluid connected to a rinse fluid input port of at least one of the first and second fluid selection valves.

4. An apparatus according to claim 3 wherein the source of rinse fluid is configured to supply water to the first fluid selection valve.

5. An apparatus according to claim 1 wherein at least one of the first and second fluid selection valves has a port fluidly configured to be connected to the analysis device via the fluid injection valve to receive a fluid evacuated from the analysis device.

6. An apparatus according to claim 1 further comprising first and second fluid pumps configured to be selectively connected by the fluid injection valve to the sample vessel such that the fluid injection valve in the first position fluidly connects the first pump to the sample vessel and the fluid injection valve in the second position fluidly connects the second pump to the sample vessel.

7. An apparatus according to claim 1 further comprising an optical device configured to optically analyze a fluid in the analysis device and determine at least one chemical characteristic thereof.

8. An apparatus according to claim 1 further comprising a processing device and a display device, the processing device being in communication with the analysis device and configured to process an output of the analysis device and display a chemical characteristic of at least one of the sample fluids on the display device.

9. An apparatus according to claim 8 wherein the processing device and the display device are electronically connected to the analysis device via a communication network.

10. An apparatus according to claim 8 wherein the processing device comprises an Ethernet port for communicating the chemical characteristic from the analysis device.

11. An apparatus according to claim 1 further comprising a bubble detector configured to detect the presence of gas in a fluid passing through the sample vessel.

12. An apparatus according to claim 1 further comprising a standard sample source fluidly connected to the first fluid selection valve and configured to supply a standard sample having a predetermined chemical characteristic.

13. A method of chemically analyzing a sample fluid, the method comprising:

adjusting a first fluid selection valve to fluidly connect a select sample input port to a sample output port such that a select sample fluid is delivered from the sample input port to the sample output port;

adjusting a fluid injection valve to a first position such that the fluid injection valve fluidly connects the sample output port to a sample vessel;

delivering the select sample fluid from the sample output port to the sample vessel;

adjusting the fluid injection valve to a second position such that the fluid injection valve fluidly connects a reagent input port to the sample vessel;

delivering a reagent fluid from the reagent input port to an analysis device via the sample vessel such that a predetermined amount of the select sample fluid is delivered to the analysis device;

mixing the select sample fluid and reagent in the analysis device; and determining at least one chemical characteristic of the select sample fluid in the analysis device.

14. A method according to claim 13 further comprising adjusting the fluid injection valve to the first position and thereby fluidly connecting the analysis device to an exhaust outlet via the sample vessel such that the select sample fluid is exhausted therefrom.

15. A method according to claim 13 further comprising adjusting the fluid injection valve to the second position and thereby fluidly connecting the sample vessel to a rinse fluid source such that the sample vessel is rinsed with a rinse fluid from the rinse fluid source.

16. A method according to claim 13 wherein said first delivering step comprises actuating a first pump and said second delivering step comprises actuating a second pump.

17. A method according to claim 13 wherein said determining step comprises detecting an optical characteristic of the select sample fluid in the analysis device.

18. A method according to claim 13 further comprising delivering an output signal of the analysis device to a processing device and displaying a chemical characteristic of the select sample fluid on a display device.

19. A method according to claim 13 further comprising communicating a signal representative of a characteristic of the select sample fluid via a communication network.

20. A method according to claim 19 wherein said communicating step comprises communicating the signal via an Ethernet port.

21. A method according to claim 13 further comprising detecting the presence of gas in a fluid passing through the sample vessel.

22. A method according to claim 13 wherein said first and second adjusting steps comprise fluidly connecting a standard sample source to the sample vessel, the standard sample source providing a standard sample having a predetermined chemical characteristic to the analysis device.

23. A method according to claim 13 wherein said second delivering step comprises delivering a predetermined amount of a fill reagent fluid to the analysis device and subsequently delivering a titration reagent fluid to the analysis device to perform a titration of the select sample fluid.

24. A method according to claim 13 further comprising repeating said second delivering step and said determining step to separately analyze first and second predetermined amounts of the select sample fluid, the chemical characteristic of the first and second predetermined amounts being substantially the same.

25. A method according to claim 24 further comprising calibrating the analysis device according to the chemical characteristic determined for the first and second predetermined amounts of the select sample fluid and a predetermined characteristic of the select sample fluid.

* * * * *